US012667565B2

(12) United States Patent
Park et al.

(10) Patent No.: US 12,667,565 B2
(45) Date of Patent: Jun. 30, 2026

(54) USE OF COMPOSITION FOR ENHANCING ANTICANCER EFFECT, COMPRISING ERRY INHIBITOR AS ACTIVE INGREDIENT

(71) Applicant: NOVMETAPHARMA CO., LTD., Seoul (KR)

(72) Inventors: Keun Gyu Park, Daegu (KR); In Kyu Lee, Daegu (KR); Sung Jin Cho, Daegu (KR); Yeon Kyung Choi, Daegu (KR); Mi Jin Kim, Daegu (KR); Jung Wook Chin, Daegu (KR); Yong Hyun Jeon, Daegu (KR); Jin A Kim, Daegu (KR); Dong Su Kim, Daegu (KR); Hoe Yune Jung, Pohang-si (KR)

(73) Assignee: NOVMETAPHARMA CO., LTD., Seoul (KR)

( * ) Notice: Subject to any disclaimer, the term of this patent is extended or adjusted under 35 U.S.C. 154(b) by 1055 days.

(21) Appl. No.: 17/779,826

(22) PCT Filed: Nov. 26, 2020

(86) PCT No.: PCT/KR2020/016976
§ 371 (c)(1),
(2) Date: May 25, 2022

(87) PCT Pub. No.: WO2021/107644
PCT Pub. Date: Jun. 3, 2021

(65) Prior Publication Data

US 2023/0017330 A1 Jan. 19, 2023

(30) Foreign Application Priority Data

Nov. 26, 2019 (KR) ........................ 10-2019-0152827

(51) Int. Cl.

| | |
|---|---|
| ***A61K 31/495*** | (2006.01) |
| ***A61K 31/44*** | (2006.01) |
| ***A61K 31/7105*** | (2006.01) |
| ***A61P 35/00*** | (2006.01) |
| ***C07K 16/28*** | (2006.01) |
| ***C12N 15/115*** | (2010.01) |
| ***G01N 33/575*** | (2026.01) |
| ***G01N 33/68*** | (2006.01) |

(52) U.S. Cl.
CPC ............ *A61K 31/495* (2013.01); *A61K 31/44* (2013.01); *A61K 31/7105* (2013.01); *A61P 35/00* (2018.01); *C07K 16/2869* (2013.01); *C12N 15/115* (2013.01); *G01N 33/5758* (2026.01); *G01N 33/6875* (2013.01)

(58) Field of Classification Search
None
See application file for complete search history.

(56) References Cited

U.S. PATENT DOCUMENTS

| | | | | |
|---|---|---|---|---|
| 6,096,874 | A | 8/2000 | Wallace et al. | |
| 10,934,303 | B2 * | 3/2021 | Hwang | C07D 203/08 |
| 11,285,226 | B2 | 3/2022 | Hwang et al. | |
| 2005/0096384 | A1 | 5/2005 | Forman et al. | |
| 2019/0161490 | A1 | 5/2019 | Hwang et al. | |
| 2019/0167820 | A1 | 6/2019 | Hwang et al. | |
| 2021/0196655 | A1 | 7/2021 | Kuo et al. | |

FOREIGN PATENT DOCUMENTS

| | | | |
|---|---|---|---|
| CN | 101836991 | A | 9/2010 |
| CN | 105331584 | A | 2/2016 |
| CN | 106255756 | A | 12/2016 |
| CN | 106466306 | A | 3/2017 |
| CN | 109055549 | A | 12/2018 |
| KR | 10-2012-0134939 | A | 12/2012 |
| KR | 10-2016-0043419 | A | 4/2016 |
| KR | 10-2017-0047827 | A | 5/2017 |
| KR | 10-2017-0079128 | A | 7/2017 |
| KR | 10-2019-0042370 | A | 4/2019 |
| KR | 10-2021-0065064 | A | 6/2021 |
| RU | 2012 148 710 | A | 5/2014 |
| WO | 2016/111507 | A1 | 7/2016 |
| WO | 2018/174506 | A1 | 9/2018 |

OTHER PUBLICATIONS

Kim, J.H. et al. Estrogen-related receptor γ is upregulated in liver cancer and its inhibition suppresses liver cancer cell proliferation via induction of p21 and p27. Exp Mol Med. Mar. 4, 2016;48(3):e213 (Year: 2016).*

Méndez-Blanco et al. Sorafenib resistance in hepatocarcinoma: role of hypoxia-inducible factors. Experimental & Molecular Medicine (2018) 50:134 (Year: 2018).*

Kim, J. et al. Exp Mol Med 48, e213 (2016). https://doi.org/10.1038/emm.2015.115 (Year: 2016).*

Ji-Hyun Kim et al., "Estrogen-related receptor γ is upregulated in liver cancer and its inhibition suppresses liver cancer cell proliferation via induction of p21 and p27", Experimental & Molecular Medicine, 2016, pp. 1-7, vol. 48, e213.

Thoudam Debraj Singh et al., "A Novel Orally Active Inverse Agonist of Estrogen-related Receptor Gamma (ERRy), DN200434, A Booster of NIS in Anaplastic Thyroid Cancer", Clinical Cancer Research, Apr. 22, 2019 (online publication date), pp. 5069-5081, vol. 25, No. 16.

Matthew G. Vander Heiden, "Targeting cancer metabolism: a therapeutic window opens", Nature Reviews | Drug Discovery, Sep. 2011, pp. 671-684, vol. 10.

(Continued)

*Primary Examiner* — Clinton A Brooks
*Assistant Examiner* — Nicola Maria Bauer
(74) *Attorney, Agent, or Firm* — Sughrue Mion, PLLC

(57) ABSTRACT

The present invention relates to a pharmaceutical composition for inhibiting the resistance of liver cancer to sorafenib and enhancing an anticancer effect, comprising an Estrogen-related receptor γ (ERRγ) inhibitor as an active ingredient. The present invention can be effectively used as a pharmaceutical composition for treating sorafenib-resistant advanced liver cancer.

7 Claims, 16 Drawing Sheets

(56) References Cited

OTHER PUBLICATIONS

Josep M. Llovet, M.D. et al., "Sorafenib in Advanced Hepatocellular Carcinoma", The New England Journal of Medicine, Jul. 24, 2008, pp. 378-390, vol. 395 No. 4.
Lorenzo Capussotti et al., "Major Liver Resections for Hepatocellular Carcinoma on Cirrhosis: Early and Long-Term Outcomes", Liver Transplantation, Feb. 2004, pp. S64-68, vol. 10, No. 2, Supple 1.
H. Lang et al., "Liver resection for hepatocellular carcinoma in non-cirrhotic liver without underlying viral hepatitis", British Journal of Surgery, 2005, pp. 198-202, vol. 92.
International Search Report for PCT/KR2020/016976, dated Mar. 15, 2021.
Notice of Allowance dated Jun. 30, 2025 in Chinese Application No. 202080082523.9.
Bo Yuan, et al., "MiR-940 inhibits hepatocellular carcinoma growth and correlates with prognosis of hepatocellular carcinoma patients", Cancer Science, Jul. 2015, vol. 106, No. 7, pp. 819-824 (6 pages total).
T.T. Berezov, et al., "Biological Chemistry," 1998, pp. 34 and 59 (4 pages total).
C.I. Pokrovsky, "Small Medical Encyclopedia," 1991, vol. 1, p. 146 (4 pages total).
Guizhi Zhu, et al., "Aptamer-based targeted therapy," Advanced Drug Delivery Reviews, 2018, pp. 1-14 (14 pages total), https://doi.org/10.1016/j.addr.2018.08.005.
O.P. Turkina, "Antisens Oligonucleotides," APRIORI, Natural and Technical Sciences, 2017, No. 3, pp. 1-15 (15 pages total), https://elibrary.ru/download/elibrary_29329867_1 6900460.pdf.
Written Opinion issued Mar. 15, 2021 in Application No. PCT/KR2020/016976.
V.G. Belikov, Pharmaceutical Chemistry, 2007, pp. 27-29 (6 pages total).
D.A. Kharkevich, Pharmacology, 2010 (7 pages total).
V.N. Zhulenko et al., Pharmacology, 2008, pp. 34-35 (4 pages total).
Kazuomi Ueshima et al., "Molecular targeted agent for hepatocellular carcinoma," Japanese Journal of Clinical Medicine, 2012, vol. 70, Suppl. 8, pp. 457-462 (8 pages total).
Jina Kim et al., "Discovery of Potent, Selective, and Orally Bioavailable Estrogen-Related Receptor-y Inverse Agonists to Restore the Sodium Iodide Symporter Function in Anaplastic Thyroid Cancer", J. Med. Chem. Jan. 18, 2019, vol. 62, pp. 1837-1858 (22 pages total).
Jens Hasskarl, "Sorafenib: targeting multiple tyrosine kinases in cancer", Recent Results Cancer Res., 2014, vol. 201 (1 page total).
International Search Report issued Sep. 18, 2023 in Application No. PCT/IB2023/055661.
Written Opinion of the International Searching Authority issued Sep. 18, 2023 in Application No. PCT/IB2023/055661.

* cited by examiner

FIG. 1C
Sora
SK-Hep
SK-Hep-R
SK-Hep
SK-Hep-R
Cleaved caspase3
Actin

Huh7-R

USE OF COMPOSITION FOR ENHANCING ANTICANCER EFFECT, COMPRISING ERRY INHIBITOR AS ACTIVE INGREDIENT

CROSS REFERENCE TO RELATED APPLICATIONS

This application is a National Stage of International Application No. PCT/KR2020/016976 filed Nov. 26, 2020, claiming priority based on Korean Patent Application No. 10-2019-0152827 filed Nov. 26, 2019.

TECHNICAL FIELD

The present invention relates to a use of a composition for enhancing an anticancer effect including an estrogen-related receptor γ (ERRγ) inhibitor as an active ingredient, and more particularly, to a pharmaceutical composition for inhibiting the resistance of liver cancer to sorafenib and enhancing an anticancer effect, including an ERRγ inhibitor as an active ingredient, a method of treating sorafenib-resistant liver cancer using the same. Also, it relates to a kit for diagnosing sorafenib-resistant liver cancer, which uses ERRγ as a biomarker for diagnosing sorafenib-resistant liver cancer, and a method of providing information for diagnosing sorafenib-resistant liver cancer using the same.

BACKGROUND ART

One of the major causes of death in Korea is a malignant neoplasm (cancer). According to the cause of death statistics published by the National Statistical Office, the death rate from liver cancer in 2016 was 21.5 per 100,000 people, which is second only to cancer mortality (Hepatocellular Carcinoma Treatment Guidelines, Korean Liver Cancer Society, 2018).

The fundamental cure for liver cancer is liver resection, which is a primary therapeutic method of treating patients with hepatocellular carcinoma confined to the liver without cirrhosis (Lang H., Liver resection for hepatocellular carcinoma in non-cirrhotic liver without underlying viral hepatitis. *Br Surg.* 2005 February 92(2): 198-202), but it can be considered first when the residual liver function is expected to be sufficient even in the presence of cirrhosis (Capussotti L, Muratore A, Massucco P, Ferrero A, Polastri R, Bouzari H Major liver resections for hepatocellular carcinoma on cirrhosis: early and long-term outcomes. *Liver Transpl.* 2004 February; 10(2 Suppl 1): S64-8), and only 30 to 40% of the patients diagnosed at an early stage can be treated surgically.

When there is extrahepatic metastasis into local lymph nodes, lungs, and the like, or when there, is hepatic vascular invasion, patients are treated using a multiple kinase inhibitor sorafenib (Nexavar®)). In this case, the degree: of improvement in survival in clinical practice falls short of an expected level, and the cancer will recur within 6 months. Thus, there is a continuing effort to overcome the disease (Llovet J M, Ricci S, Mazzaferro V, Hilgard P, Gane E, Blanc J F, de Oliveira A C, et al., Sorafenib in advanced hepatocellular carcinoma. *N Engl J Med* 2008; 359: 378-390).

Meanwhile, research on cancer metabolism and new drug development is being conducted to overcome the limitations of the existing anticancer drugs or target therapeutic agents and to target the metabolic characteristics of cancer by studying the specific metabolic control of cancer cells other than normal cells (Vander Heiden M G. Targeting cancer metabolism: a therapeutic window opens. *Nat Rev Drug Discov* 2011; 10: 671-684).

RELATED-ART DOCUMENT

Patent Document

Patent Document 1: Korean Patent Publication No. 10-1704533

DISCLOSURE

Technical Problem

Accordingly, the present inventors have found that an ERRγ inhibitor inhibits the resistance of liver cancer to sorafenib and effectively inhibits the proliferation of liver cancer. Therefore, the present invention has been completed based on this finding.

Therefore, it is one object of the present invention to provide a pharmaceutical composition for preventing or enhancing the treatment of sorafenib-resistant liver cancer, which includes an ERRγ inhibitor as an active ingredient.

It is another object of the present invention to provide a pharmaceutical composition for inhibiting sorafenib resistance in liver cancer, which includes an ERRγ inhibitor as an active ingredient.

It is still another object of the present invention to provide a pharmaceutical composition for preventing or treating liver cancer, which includes an ERRγ inhibitor and sorafenib as active ingredients.

It is yet another object of the present invention to provide a method of screening a material that enhances the treatment of sorafenib-resistant liver cancer, which includes treating sorafenib-resistant liver cancer cells with a candidate material; and evaluating the activity or expression of ERRγ in the cells.

It is yet another object of the present invention to provide a kit for diagnosing sorafenib-resistant liver cancer, which includes an agent for measuring a level of mRNA of an estrogen-related receptor γ (ERRγ) gene or a protein expressed therefrom.

It is yet another object of the present invention to provide a method of providing information for diagnosis of sorafenib-resistant liver cancer, including the following steps:

(a) measuring an expression level of mRNA of an ERRγ gene or a protein expressed therefrom in a biological sample isolated from a liver cancer patient to check whether liver cancer exhibits resistance to sorafenib;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

It is yet another object of the present invention to provide a method of providing information required to determine a therapeutic method for a liver cancer patient, which includes the following steps:

(a) measuring an expression level of mRNA of an ERRγ gene or a protein expressed therefrom in a biological sample isolated from the liver cancer patient;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

It is yet another object of the present invention to provide a method of diagnosing or treating sorafenib-resistant liver cancer, which includes the following steps:

(a) measuring an expression level of mRNA of an ERRγ gene or a protein expressed therefrom in a biological sample isolated from a liver cancer patient;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer and applying another liver cancer therapeutic agent other than sorafenib when the expression level of the mRNA of the ERRγ gene or the protein expressed therefrom measured in step (a) is higher than the expression level of the mRNA of the ERRγ gene or the protein expressed therefrom measured in step (b).

It is yet another object of the present invention to provide a method of preventing or enhancing the treatment of sorafenib-resistant liver cancer, which includes administering an ERRγ inhibitor to the patient with sorafenib-resistant liver cancer.

It is yet another object of the present invention to provide a method of inhibiting sorafenib resistance in liver cancer, which includes administering an ERRγ inhibitor to the patient with sorafenib-resistant liver cancer.

It is yet another object of the present invention to provide a method of preventing or treating liver cancer, which includes administering an ERRγ inhibitor and sorafenib to a liver cancer patient.

However, the technical objects to be achieved in the present invention are not limited to the above-described technical objects, and thus it should be understood that technical objects which are not described in this specification will be made apparent from the detailed description of the invention by those skilled in the art.

Technical Solution

To achieve the above objects, according to an aspect of the present invention, there is provided an agent capable of inhibiting estrogen-related receptor γ (ERRγ) protein activity or ERRγ gene expression for use in preventing or enhancing the treatment of sorafenib-resistant liver cancer.

In this regard, according to another aspect of the present invention, there is provided a pharmaceutical composition for preventing or enhancing the treatment of sorafenib-resistant liver cancer, which includes the ERRγ inhibitor as an active ingredient.

According to still another aspect of the present invention, there is provided a method of preventing or enhancing the treatment of sorafenib-resistant liver cancer, which includes administering the ERRγ inhibitor to a subject.

According to yet another aspect of the present invention, there is provided a use of the ERRγ inhibitor for preventing, ameliorating, or enhancing the treatment of sorafenib-resistant liver cancer.

According to one embodiment of the present invention, the agent for inhibiting ERRγ protein activity may be an inverse agonist or an antagonist against ERRγ, or an antibody or an aptamer capable of specifically binding to ERRγ, but the present invention is not limited thereto.

According to one embodiment of the present invention, the inverse agonist against ERRγ may be a compound represented by the following Formula 1 or a pharmaceutically acceptable salt thereof, but is not limited to the compound as long as it is an inverse agonist against ERRγ that exhibits an effect equivalent to the compound.

[Formula 1]

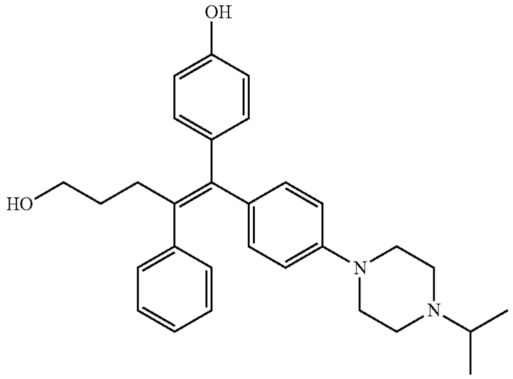

According to another embodiment of the present invention, the agent for inhibiting the expression of the ERRγ gene may be selected from the group consisting of miRNA, siRNA, shRNA, and an antisense oligonucleotide, all of which specifically bind to mRNA of the gene, but the present invention is not limited thereto.

According to yet another aspect of the present invention, there is provided an agent capable of inhibiting ERRγ protein activity or ERRγ gene expression for use in inhibiting the resistance to sorafenib in the prevention or treatment of liver cancer.

In this regard, according to yet another aspect of the present invention, there is provided a pharmaceutical composition for inhibiting sorafenib resistance in liver cancer, which includes the ERRγ inhibitor as an active ingredient.

According to yet another aspect of the present invention, there is provided a method of inhibiting sorafenib resistance in liver cancer, which includes administering the ERRγ inhibitor to a subject.

According to yet another aspect of the present invention, there is provided a use of the ERRγ inhibitor for inhibiting the resistance of liver cancer to sorafenib.

According to yet another aspect of the present invention, there is provided a composition including an agent capable of inhibiting ERRγ protein activity or ERRγ gene expression for use in the prevention or treatment of liver cancer.

In this regard, according to yet another aspect of the present invention, there is provided a pharmaceutical composition for preventing or treating liver cancer, which includes the ERRγ inhibitor; and sorafenib as active ingredients.

According to yet another aspect of the present invention, there is provided a method of preventing or treating liver cancer, which includes administering the composition including ERRγ inhibitor and sorafenib as active ingredients to a subject.

According to yet another aspect of the present invention, there is provided a use of the composition, which includes the ERRγ inhibitor and sorafenib as active ingredients, for preventing, ameliorating, or enhancing the treatment of liver cancer.

According to one embodiment of the present invention, the composition may enhance the drug susceptibility of liver cancer to sorafenib or may enhance an anticancer effect of sorafenib on liver cancer, but the present invention is not limited thereto.

According to still another embodiment of the present invention, the composition may be administered simultaneously with sorafenib, separately, or sequentially, but the present invention is not limited thereto.

According to yet another aspect of the present invention, there is provided a method of screening a material that enhances the treatment of sorafenib-resistant liver cancer, which includes treating sorafenib-resistant liver cancer cells with a candidate material; and evaluating the activity or expression of ERRγ in the cells.

According to yet another aspect of the present invention, there is provided a kit for diagnosing sorafenib-resistant liver cancer, which includes an agent for measuring a level of mRNA of an estrogen-related receptor γ (ERRγ) gene or a protein expressed therefrom.

According to one embodiment of the present invention, the agent for measuring a level of mRNA of the gene may include a pair of primers, a probe, or an antisense nucleotide, which specifically binds to the gene, but the present invention is not limited thereto.

According to yet another embodiment of the present invention, the agent for measuring a level of the protein may include an antibody or an aptamer specific for the protein, but the present invention is not limited thereto.

According to yet another embodiment of the present invention, the kit may include an RT-PCR kit, a competitive RT-PCR kit, a real-time RT-PCR kit, a DNA chip kit, or a protein chip kit, but the present invention is not limited thereto.

According to yet another aspect of the present invention, there is provided a method of providing information for diagnosis of sorafenib-resistant liver cancer, including the following steps:

(a) measuring an expression level of mRNA of an ERRγ gene or a protein expressed therefrom in a biological sample isolated from a liver cancer patient to check whether liver cancer exhibits resistance to sorafenib;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

According to yet another aspect of the present invention, there is provided a method of providing information required to determine a therapeutic method for a liver cancer patient, including the following steps:

(a) measuring an expression level of mRNA of an ERRγ gene or a protein expressed therefrom in a biological sample isolated from the liver cancer patient;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

According to yet another aspect of the present invention, there is provided a method of diagnosing and treating sorafenib-resistant liver cancer, including the following steps:

(a) measuring an expression level of mRNA of an ERRγ gene or a protein expressed therefrom in a biological sample isolated from a liver cancer patient;

(b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer and applying another liver cancer therapeutic agent other than sorafenib when the expression level of the mRNA of the ERRγ gene or the protein expressed therefrom measured in step (a) is higher than the expression level of the mRNA of the ERRγ gene or the protein expressed therefrom measured in step (b).

According to one embodiment of the present invention, the biological sample may include liver tissue, liver cells, whole blood, plasma, serum, or blood, but the present invention is not limited thereto.

Advantageous Effects

According to the present invention, an estrogen-related receptor γ (ERRγ) inhibitor has an effect of enhancing the susceptibility to the anticancer drug sorafenib, inhibiting the proliferation of sorafenib-resistant liver cancer cells, and significantly reducing the size of liver cancer. Therefore, the present invention is expected to be effectively used as a pharmaceutical composition for treating advanced sorafenib-resistant liver cancer. Also, through the method of providing information for diagnosis of sorafenib-resistant liver cancer according to the present invention, it is possible to predict the therapeutic responsiveness of liver cancer patients to sorafenib and thus to establish a therapeutic strategy, for each patient based on the prediction results, thereby effectively treating liver cancer.

BEST MODE

Figure 1A:
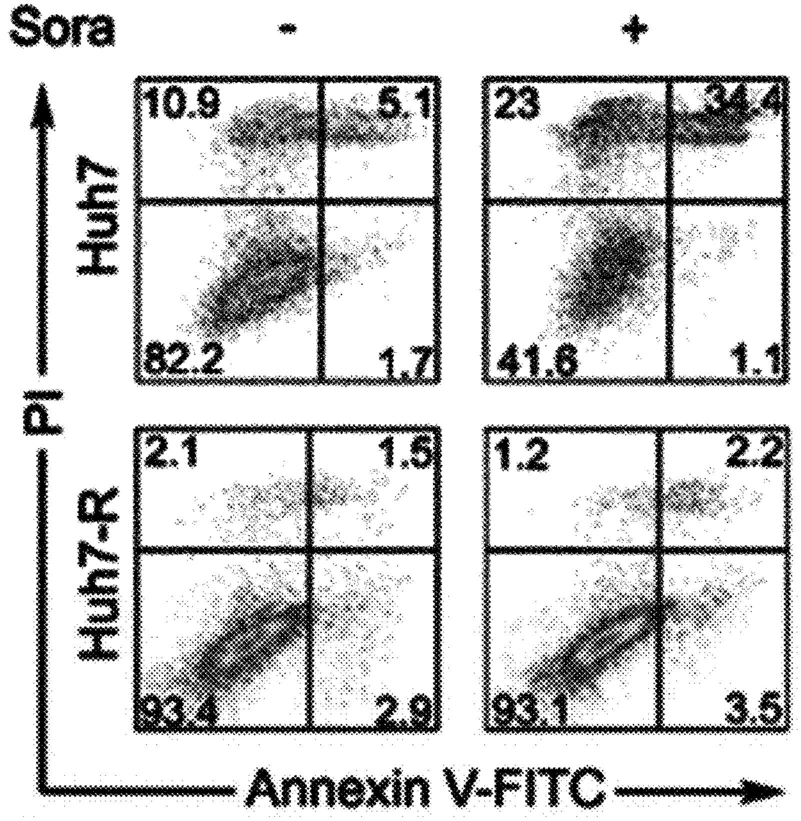
FIGS. 1A to 1C are diagrams showing the results of constructing a liver cancer cell line exhibiting resistance to sorafenib (Huh7: liver cancer cell line; Huh7-R: sorafenib-resistant liver cancer cell line; SK-Hep: liver cancer cell line; SK-Hep-R: sorafenib-resistant liver cancer cell line).

The present invention provides an agent capable of inhibiting estrogen-related receptor γ (ERRγ) protein activity or ERRγ gene expression for use in preventing or enhancing the treatment of sorafenib-resistant liver cancer.

In this regard, the present invention provides a pharmaceutical composition for preventing or enhancing the treatment of sorafenib-resistant liver cancer, which includes, as an active ingredient, the agent capable of inhibiting ERRγ protein activity or ERRγ gene expression.

According to another aspect of the present invention, the present invention provides an agent capable of inhibiting ERRγ protein activity or ERRγ gene expression for use in inhibiting the resistance to sorafenib in the prevention or treatment of liver cancer.

In this regard, the present invention provides a pharmaceutical composition for inhibiting sorafenib resistance in liver cancer, which includes as an active ingredient the agent capable of inhibiting ERRγ protein activity or ERRγ gene expression.

According to still another aspect of the present invention, the present invention provides a composition including the agent capable of inhibiting ERRγ protein activity or ERRγ gene expression for use in the prevention or treatment of liver cancer.

In this regard, the present invention provides a pharmaceutical composition for preventing or treating liver cancer, which includes, as active ingredients, the agent capable of inhibiting ERRγ protein activity or ERRγ gene expression; and sorafenib.

As used in this specification, the term "liver cancer" refers to a primary malignant tumor that occurs primarily in the liver. In a pathological (historical) aspect, the primary malignant tumor includes various types of primary liver cancer such as hepatocellular carcinoma, cholangiocarcinoma, hepatoblastoma, and hemangiosarcoma. Among them, hepatocellular carcinoma and cholangiocarcinoma account for the majority of the primary liver cancer.

In the present invention, the liver cancer may be hepatocellular carcinoma (HCC), but the present invention is not limited thereto.

As used in this specification, the term "enhancing the treatment of" refers to all types of actions for improving or beneficially changing the symptoms of sorafenib-resistant liver cancer by administration of the pharmaceutical composition of the present invention after liver cancer has acquired resistance to sorafenib.

As used in this specification, the term "treatment" refers to all types of actions for improving or beneficially changing the symptoms for liver cancer by administration of the pharmaceutical composition of the present invention before or after liver cancer has acquired resistance to sorafenib.

In the present invention, the pharmaceutical composition of the present invention may enhance the drug susceptibility to sorafenib or may enhance an anticancer effect of sorafenib on liver cancer, but the present invention is not limited thereto.

According to one embodiment of the present invention, a Huh7-SR or SK-Hep-R cell line was constructed as a sorafenib-resistant liver cancer cell line, and it was confirmed that estrogen-related receptor γ (ERRγ) as an orphan nuclear receptor remarkably increases in a liver cancer cell line acquiring resistance to sorafenib (see Example 1).

Also, according to one embodiment of the present invention, it was confirmed that, when sorafenib-resistant liver cancer cells are treated with the compound (DN200434) represented by Formula 1, which is an inverse agonist against ERRγ, ROS increases. Also, it was confirmed that the sorafenib-resistant liver cancer cells which did not have an anticancer effect when the cell lines are treated with sorafenib alone have reduced cell proliferation when the cell lines are treated with the compound (DN200434) represented by Formula 1 and sorafenib at the same time. As a result, it was confirmed that the compound represented by Formula 1 increases the susceptibility to sorafenib by inhibiting ERRγ activity, thereby exhibiting an effect of overcoming drug resistance (see Example 2).

In addition, according to one embodiment of the present invention, it was confirmed that, when a change in size of a mass formed after the compound represented by Formula 1 is administered in combination with sorafenib in an animal model derived from sorafenib-resistant liver cancer is measured, the size of liver cancer remarkably decreases, compared to the control (a sorafenib-alone-treated group) (see Example 3).

In the present invention, the agent for inhibiting ERRγ protein activity may be an inverse agonist or an antagonist against ERRγ, or an antibody or an aptamer capable of specifically binding to ERRγ, but the present invention is not limited thereto.

As used in this specification, the term “inverse agonist” or “antagonist” refers to a molecule capable of directly or indirectly reducing the biological activity of a receptor, and includes molecules capable of reducing the action of a ligand when used in conjunction with the ligand of the receptor, but the present invention is not limited thereto.

As used in this specification, the term “antibody” refers to a proteinaceous molecule capable of specifically binding to an antigenic site of a protein or peptide molecule. In this case, a protein encoded by the marker gene may be obtained by cloning each gene into an expression vector according to a conventional method, and such an antibody may be prepared from the obtained protein using a conventional method.

As used in this specification, the term “aptamer” refers to a nucleic acid molecule that has binding activity for a predetermined target molecule. The aptamer may be RNA, DNA, a modified nucleic acid, or a mixture thereof, and may be in a linear or cyclic form. In general, chemical synthesis and mass production may be easier as the nucleotide sequence constituting the aptamer gets shorter and it is known that the aptamer has an excellent advantage in terms of costs, is easily chemically modified, and exhibits excellent in vivo stability and low toxicity.

The inverse agonist and the antagonist may be a compound.

In the present invention, the inverse agonist against ERRγ may be a compound represented by the following Formula 1 or a pharmaceutically acceptable salt thereof, but the present invention is not limited thereto.

[Formula 1]

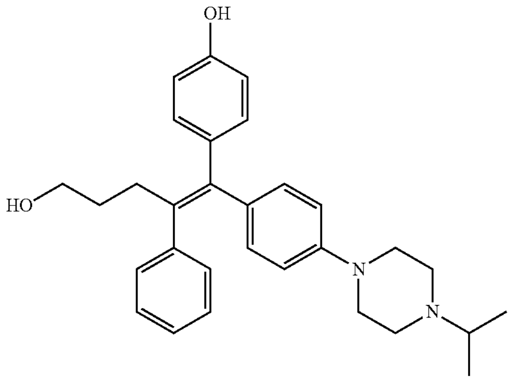

As used in this specification, the term “pharmaceutically acceptable” is suitable for use in contact with the tissue of a subject (e.g., a human) because the benefit/risk ratio is reasonable without undue toxicity, irritation, allergic reactions, or other problems or complications. In this case, the term refers to a compound or composition that falls within the scope of sound medical judgment.

The compound of the present invention may be used in the form of a pharmaceutically acceptable salt. In this case, an acid addition salt formed by a pharmaceutically acceptable free acid may be used as the salt.

The acid addition salt may be obtained from inorganic acids such as hydrochloric acid, nitric acid, phosphoric acid, sulfuric acid, hydrobromic acid, hydroiodic acid, nitrous acid, or phosphorous acid, and aliphatic mono- and dicarboxylates, phenyl-substituted alkanoates, hydroxy alkanoates, and alkanedioates, and non-toxic organic acids such as aromatic acids, aliphatic and aromatic sulfonic acids, and the like.

Such a pharmaceutically non-toxic salt includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, (3-hydroxybutyrate, glycolate, malate, tartrate, methanesulfonate, propanesulfonate, naphthalene-1-sulfonate, naphthalene-2-sulfonate, or mandelate.

The acid addition salt according to the present invention may be prepared by a conventional method, for example, by dissolving the compound of Formula 1 in an aqueous acid solution, and precipitating the salt in a water-miscible organic solvent such as methanol, ethanol, acetone, or acetonitrile. Also, the acid addition salt may be prepared by evaporating the solvent or excess acid from the mixture and drying the mixture, or by filtering the precipitated salt by suction.

Also, a pharmaceutically acceptable metal salt may be prepared using a base. An alkali metal or alkaline earth metal salt is obtained, for example, by dissolving the compound of Formula 1 in an excess alkali metal hydroxide or alkaline earth metal hydroxide solution, filtering the undissolved compound salt, and evaporating and drying the filtrate. In this case, it may be pharmaceutically suitable to prepare a sodium, potassium, or calcium salt as the metal salt. A silver salt corresponding to the metal salt is obtained by reacting an alkali metal or alkaline earth metal salt with a suitable silver salt (e.g., silver nitrate).

All isomers, hydrates and solvates that can be prepared by conventional methods, as well as pharmaceutically acceptable salts thereof, may be included in the scope of the compound of the present invention.

In the present invention, the agent for inhibiting ERRγ gene expression may be selected from the group consisting of miRNA, siRNA, shRNA, and an antisense oligonucleotide, all of which specifically bind to mRNA of the gene, but the present invention is not limited thereto.

As used in this specification, the terms “miRNA,” “siRNA,” and “shRNA” refer to nucleic acid molecules that mainly bind to mRNA transcribed from a target gene to mediate RNA interference or gene silencing, thereby inhibiting the translation of mRNA. Because the miRNA, siRNA, and shRNA may inhibit the expression of the target gene at a translational level, they can be used in an efficient gene knockdown method or gene therapy method.

As used in this specification, the term "antisense oligonucleotide" refers to a DNA or RNA or a derivative thereof containing a nucleic acid sequence complementary to a specific mRNA sequence. In this case, the antisense oligonucleotide may bind to a complementary sequence in mRNA, thereby inhibiting the translation of mRNA into a protein.

Meanwhile, the pharmaceutical composition according to the present invention may further include an appropriate carrier, excipient and/or diluent commonly used to prepare a pharmaceutical composition in addition to the active ingredient. Also, the pharmaceutical composition may be formulated in the form of oral formulations such as powders, granules, tablets, capsules, suspensions, emulsions, syrups, aerosols, and the like, preparations for external use, suppositories, and sterile injectable solutions, and may be used according to conventional methods.

The carrier, excipient, and diluent that may be included in the composition include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oils, and the like. When the composition is formulated, a formulation may be manufactured using a diluent or excipient such as a filler, an extender, a binder, a wetting agent, a disintegrant, a surfactant, and the like commonly used in the art.

The pharmaceutical composition according to the present invention is administered in a pharmaceutically effective amount. In the present invention, the term "pharmaceutically effective amount" refers to an amount sufficient to treat a disease at a reasonable benefit/risk ratio applicable to medical treatment, and an effective dose level may be determined depending on the type and severity of a patient's disease, the activity of a drug, the sensitivity to a drug, an administration time, a route of administration, and an excretion rate, a treatment period, factors including concurrently used drugs, and other factors well known in the medical field.

In the present invention, the pharmaceutical composition of the present invention may be administered simultaneously with sorafenib, separately, or sequentially, and may be administered in single or multiple doses.

In consideration of all of the above factors, it is important to administer an amount that can obtain the maximum effect with a minimum amount without any side effects, which can be determined by a person skilled in the art. Specifically, the effective amount of the pharmaceutical composition according to the present invention may vary depending on the age, sex, condition, and weight of a patient, the absorption of an active ingredient into the body, an inactivation rate and an excretion rate, the type of disease, and concurrently used drugs.

The pharmaceutical composition of the present invention may be administered to a subject through various routes of administration. For example, the pharmaceutical composition may be administered by oral administration, intranasal administration, transbronchial administration, arterial injection, intravenous injection, subcutaneous injection, intramuscular injection or intraperitoneal injection. The daily dosage may be administered once or multiple times a day.

According to another aspect of the present invention, the present invention provides a method for preventing or enhancing the treatment of sorafenib-resistant liver cancer, which includes administering an ERRγ inhibitor to a subject.

Specifically, there is provided a method of preventing or enhancing the treatment of sorafenib-resistant liver cancer, which includes administering an ERRγ inhibitor to a patient with sorafenib-resistant liver cancer.

According to still another aspect of the present invention, the present invention also provides a method of inhibiting sorafenib resistance in liver cancer, which includes administering an ERRγ inhibitor to a subject.

Specifically, there is provided a method of inhibiting sorafenib resistance in liver cancer, which includes administering an ERRγ inhibitor to a patient with sorafenib-resistant liver cancer.

According to yet another aspect of the present invention, the present invention provides a method of preventing or treating liver cancer, which includes administering a composition including an ERRγ inhibitor and sorafenib as active ingredients to a subject.

Specifically, there is provided a method of preventing or treating liver cancer, which includes administering the ERRγ inhibitor and sorafenib to a liver cancer patient.

In the method of the present invention, the liver cancer may be sorafenib-resistant liver cancer, but the present invention is not limited thereto.

As used in this specification, the term "subject" refers to a subject in need of prevention, treatment, enhancement of the treatment of a disease, or inhibition of resistance in the disease. For example, the subject may include humans, or mammals including non-human primates, mice, dogs, cats, horses, sheep, and cattle.

According to yet another aspect of the present invention, the present invention also provides a method of screening a material that enhances the treatment of sorafenib-resistant liver cancer, which includes (a) treating sorafenib-resistant liver cancer cells with a candidate material; and (b) evaluating the activity or expression of ERRγ in the cells. A material capable of inhibiting the activity or expression of ERRγ in sorafenib-resistant liver cancer cells may be selected through such a method, and may be used as an enhancer or adjuvant for treatment of sorafenib-resistant liver cancer.

According to yet another aspect of the present invention, the present invention provides a kit for diagnosing sorafenib-resistant liver cancer.

Specifically, the kit for diagnosing sorafenib-resistant liver cancer includes an agent for measuring a level of mRNA of an ERRγ gene or a protein expressed therefrom.

In the present invention, the term "diagnosis" means confirming the presence or characteristics of a pathological condition. In the present invention, the diagnosis is to determine the presence or occurrence of sorafenib-resistant liver cancer by measuring a level of mRNA of an ERRγ gene or a protein expressed therefrom.

As used in the present invention, the term "an agent for measuring an expression level of mRNA of an ERRγ gene or a protein thereof" refers to a molecule that may be used to check an expression level of an ERRγ gene or a protein encoded by such a gene. In this case, the agent may preferably be a pair of primers, a probe, or an antisense nucleotide, all of which specifically bind to the ERRγ gene, or may be an antibody or an aptamer specific for a protein encoded by the ERRγ gene.

In the present invention, the term "primer" refers to a short nucleic acid sequence having a free 3' hydroxyl group, that is, a short nucleic acid sequence that may form a base pair with a complementary template and serves as a starting point for copying the template. In the present invention, PCR amplification may be performed using sense and antisense primers of a marker polynucleotide according to the present invention to screen patients with sorafenib-resistant liver cancer through the production level of the desired product. The PCR conditions, the length of the sense and antisense primers can be modified based on what is known in the art.

As used in the present invention, the term "probe" refers to a nucleic acid fragment such as RNA or DNA corresponding to several bases to several hundred bases that may specifically bind to mRNA, and may be labeled to determine the presence/absence of specific mRNA. The probe may be manufactured in the form of an oligonucleotide probe, a single-stranded DNA probe, a double-stranded DNA probe, an RNA probe, and the like. In the present invention, hybridization may be performed using a probe complementary to the ERRγ polynucleotide of the present invention in order to screen patients with sorafenib-resistant liver cancer based on the degree of hybridization. The selection of suitable probes and the hybridization conditions can be modified based on what is known in the art.

The primers or probes of the present invention may be chemically synthesized using a phosphoramidite solid support method or other well-known methods. Such nucleic acid sequences may also be modified using a number of means known in the art. Non-limiting examples of such modifications include methylation, encapsulation, substitution of one or more homologs of a natural nucleotide, and internucleotide modifications such as modifications into uncharged linkages (e.g., methyl phosphonate, phosphotriester, phosphoramidate, carbamate, etc.) or charged linkages (e.g., phosphorothioate, phosphorodithioate, etc.).

A nucleotide sequence of the agent for measuring an expression level of the ERRγ gene used in the present invention is interpreted to include a sequence that exhibits substantial identity with a sequence specifically binding to the ERRγ gene in consideration of the mutations having biologically equivalent activity. The term "substantial identity" refers to a sequence that exhibits an identity of at least 60%, more specifically an identity of 70%, even more specifically an identity of 80%, and most specifically an identity of 90% when a specific sequence and any other sequence are aligned to the maximum possible correspondence and the aligned sequence is analyzed using an algorithm commonly used in the art.

In the kit of the present invention, the terms "antibody" and "aptamer" are the same as described in the pharmaceutical composition, and thus a description thereof will be omitted.

The kit of the present invention may be used to diagnose sorafenib-resistant liver cancer by checking an mRNA expression level of the ERRγ gene or an expression level of a protein encoded by the gene, or used to predict the therapeutic response to sorafenib.

Because the kit of the present invention may be used to predict the therapeutic response to sorafenib, the kit may also be used for predicting the prognosis of liver cancer patients.

In the present invention, the term "predicting the prognosis of" refers to a process of guessing about a medical consequence in advance, and for the purpose of the present, means presuming the resistance of liver cancer patients to sorafenib.

According to one embodiment of the present invention, the kit may be an RT-PCR kit, a competitive RT-PCR kit, a real-time RT-PCR kit, a DNA chip kit, or a protein chip kit, but the present invention is not limited thereto.

According to one embodiment of the present invention, the kit for measuring an expression level of mRNA of the ERRγ gene may be a kit including essential elements necessary for performing RT-PCR. In addition to each pair of primers specific for a marker gene, the RT-PCR kit contains test tubes or other suitable containers, a reaction buffer, deoxynucleotides (dNTPs), a Taq-polymerase and a reverse transcriptase, DNase, an RNase inhibitor, DEPC-water, sterile water, and the like.

The kit of the present invention may include a kit for extracting a nucleic acid (e.g., total RNA) from a body fluid, cells, or tissue, a fluorescent substance for labeling, an enzyme and medium for nucleic acid amplification, instructions for use, and the like.

According to another embodiment of the present invention, the kit of the present invention may be a kit for detecting ERRγ including essential elements necessary for using a DNA chip. The DNA chip kit may include a substrate to which cDNA corresponding to a gene or a fragment thereof is attached as a probe, and the substrate may include cDNA corresponding to a quantitative control gene or a fragment thereof.

According to still another embodiment of the present invention, the kit for measuring an expression level of the protein encoded by ERRγ according to the present invention may include a substrate for immunological detection of an antibody, a suitable buffer solution, a secondary antibody labeled with a chromogenic enzyme or a fluorescent substance, a chromogenic substrate, and the like. In this case, a nitrocellulose membrane, a 96-well plate synthesized from polyvinyl resin, a 96-well plate synthesized from polystyrene resin, and a glassy slide glass may be used as the substrate. A peroxidase and an alkaline phosphatase may be used as the chromogenic enzyme. FITC, RITC, and the like may be used as the fluorescent material, and ABTS (2,2'-azino-bis-(3-ethylbenzothiazoline-6-sulfonic acid)), OPD (o-phenylenediamine), TMB (tetramethyl benzidine), and the like may be used as the chromogenic substrate.

The kit of the present invention may be configured to further include a composition, a solution or a device having one or more other components suitable for an analysis method.

According to still another aspect, the present invention provides a method of providing information for diagnosis of sorafenib-resistant liver cancer.

Specifically, the method of providing information for diagnosis of sorafenib-resistant liver cancer includes: (a) measuring an expression level of mRNA of an ERRγ gene or a protein expressed therefrom in a biological sample isolated from a liver cancer patient to check whether liver cancer exhibits resistance to sorafenib; (b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

In the present invention, the term "biological sample" refers to a tissue (liver tissue), cells (liver cells), whole blood, plasma, serum, blood, saliva, synovial fluid, urine, sputum, lymph fluid, cerebrospinal fluid, tissue autopsy samples (brain, skin, lymph nodes, spinal cord, or the like), a cell culture supernatant, or ruptured eukaryotic cells, which have different expression and/or activity levels of ERRγ as a sorafenib-resistant liver cancer marker. Also, the biological sample includes samples derived from metastatic lesions as well as primary cancer lesions. In this case, the activity or expression level of ERRγ may be determined in a state in which these biological samples are manipulated or not manipulated.

In the method of providing information for diagnosis of sorafenib-resistant liver cancer according to the present invention, the biological sample of step (a) may be obtained using a specific method known to those skilled in the art. For example, the biological sample may be obtained from a vertebrate, particularly a mammal, and may be preferably obtained from a liver cancer patient to check whether liver cancer exhibits resistance to sorafenib. In this case, the liver cancer patient is a human. A tissue biopsy is often used to obtain a representative piece of tumor tissue. Alternatively, the tumor cells may be indirectly obtained in the form of a tissue or a fluid known or believed to contain the tumor cells of interest.

In the present invention, the term "measuring an expression level of mRNA" refers to a process of confirming the presence and expression level of mRNA of the ERRγ gene in a biological sample, and may be known by measuring an amount of mRNA. Analysis methods for this include RT-PCR, competitive RT-PCR, real-time RT-PCR, an RNase protection method, northern blotting, or DNA chip technology, but the present invention is not limited thereto.

In the present invention, the term "measuring an expression level of a protein" refers to a process of confirming the presence and expression level of a protein expressed from the ERRγ gene in a biological sample. In this case, an amount of the protein may be determined using an antibody specifically binding to the protein expressed from the gene. Analysis methods for this include Western blotting, an enzyme linked immunosorbent assay (ELISA), a radioimmunoassay (RIA), radial immunodiffusion, Ouchterlony immunodiffusion, rocket immunoelectrophoresis, immunohistochemical staining, an immunoprecipitation assay, a complement fixation assay, immunofluorescence, immunochromatography, fluorescence-activated cell sorter analysis (FACS analysis), protein chip technology, or the like, but the present invention is not limited thereto.

In the method of providing information for diagnosis of sorafenib-resistant liver cancer according to the present invention, a patient with general liver cancer other than sorafenib-resistant liver cancer may be a patient with hepatocellular carcinoma (HCC) or hepatic adenocarcinoma who does not exhibit sorafenib-resistant liver cancer, but the present invention is not limited thereto.

In the method of providing information for diagnosis of sorafenib-resistant liver cancer according to the present invention, the expression level of the ERRγ gene may be measured at an mRNA level or a protein level, and the isolation of the mRNA or the protein from the biological sample may be performed using a process known in the art. An analysis method of measuring an mRNA level and an analysis method of measuring a protein level are as described above.

Through the method of providing information for diagnosis of sorafenib-resistant liver cancer according to the present invention, it is possible to predict the therapeutic response of liver cancer patients to sorafenib and establish a treatment strategy for each patient based on the prediction results, thereby making it possible to effectively treat liver cancer.

Therefore, according to yet another aspect, the present invention provides a method of providing information required to determine a therapeutic method for a liver cancer patient, which includes measuring an expression level of mRNA of an ERRγ gene or a protein expressed therefrom in a biological sample isolated from a liver cancer patient.

Specifically, the method of providing information required to determine a therapeutic method for a liver cancer patient may include: (a) measuring an expression level of mRNA of an ERRγ gene or a protein expressed therefrom in a biological sample isolated from the liver cancer patient; (b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer when the expression level of the mRNA of the ERRγ gene or the protein expressed therefrom measured in step (a) is higher than the expression level of the mRNA of the ERRγ gene or the protein expressed therefrom measured in step (b).

According to the method of providing information required to determine a therapeutic method for a liver cancer patient, when resistance to sorafenib is confirmed in the liver cancer patient, a liver cancer treatment effect may be induced by applying other known liver cancer therapeutic agents other than sorafenib.

Therefore, according to a further aspect, the present invention provides a method of diagnosing and treating sorafenib-resistant liver cancer.

Specifically, the method for diagnosing and treating sorafenib-resistant liver cancer according to the present invention includes: (a) measuring an expression level of mRNA of an ERRγ gene or a protein expressed therefrom in a biological sample isolated from a liver cancer patient; (b) measuring an expression level of mRNA of an ERRγ gene or a protein expressed therefrom in a biological sample isolated from a patient with general liver cancer other than sorafenib-resistant liver cancer; and (c) judging the liver cancer patient in step (a) to be a patient with sorafenib-resistant liver cancer and applying another liver cancer therapeutic agent other than sorafenib when the expression level of the mRNA of the ERRγ gene or the protein expressed therefrom measured in step (a) is higher than the expression level of the mRNA of the ERRγ gene or the protein expressed therefrom measured in step (b).

Specific details of the method for providing information required to determine a therapeutic method for a liver cancer patient and/or the method of diagnosing and treating sorafenib-resistant liver cancer according to the present invention are as described above in the method of providing information for diagnosis of sorafenib-resistant liver cancer, and a description thereof will be omitted.

It should be understood that the terms and words used in the specification and the appended claims should not be construed as being limited to general and dictionary meanings, but interpreted based on the meanings and concepts corresponding to technical aspects of the present invention on the basis of the principle that the present inventors can appropriately define the concepts of terms to describe the present invention in the best way.

Hereinafter, preferred embodiments are provided to aid in understanding the present invention. However, it should be understood that the following examples are merely intended to provide a better understanding of the present invention, and are not intended to limit the scope of the present invention.

MODE FOR INVENTION

Experimental Examples

General Experimental Methods

The present inventors have performed experiments using sorafenib-resistant liver cancer cell lines (Huh7-SR and SK-Hep-R cell lines) and a liver cancer cell line-derived animal model (xenograft). To determine an effect of the synthetic compound DN200434, which is an inverse agonist against ERRγ, on the proliferation of liver cancer cells and ROS generation, ROS was measured using a cell count and 2',7-dichlorofluorescin diacetate (DCF-DA). Finally, after a sorafenib-resistant liver cancer cell line was injected into rats to induce the formation of sorafenib-resistant liver cancer, changes in size of liver cancer were confirmed in the group injected with the inverse agonist against ERRγ (DN200434) and sorafenib and the group injected with the control drug.

Example 1

Figure 1B:
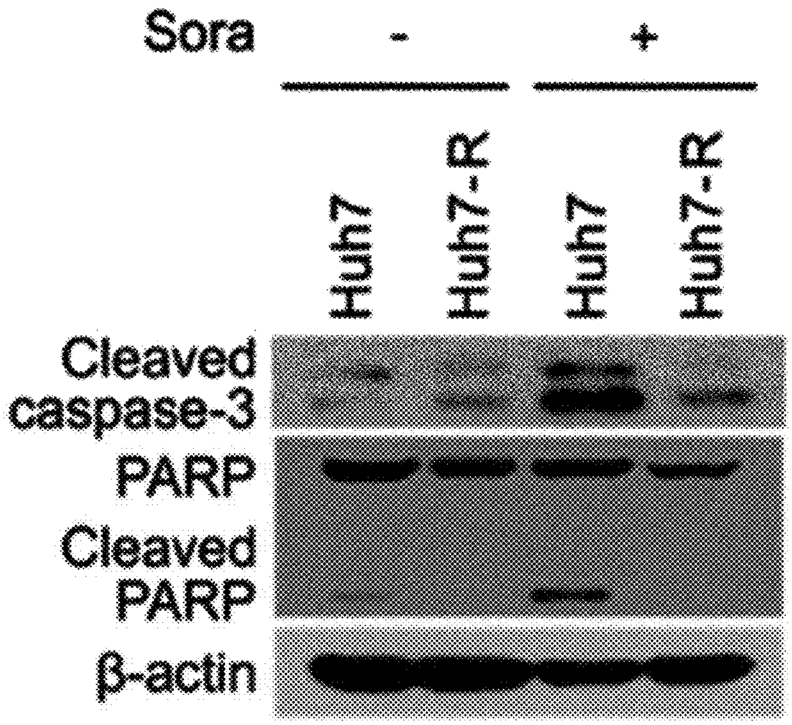
Figure 1C:

Construction of Sorafenib-Resistant Liver Cancer Cell Line and Confirmation of Increased ERRγ Expression Hepatocarcinoma cell lines [Huh7 cells (Korea Cell Line Bank (KCLB) No. 60104), SK-Hep cells (ATCC® HTB-52™)] were continuously exposed to sorafenib (gradually increasing to 10 μM) to construct sorafenib-resistant liver cancer cell lines (Huh7-SR and SK-Hep-R cell lines). To evaluate the cancer cell death by FACS, first, a cancer cell line was incubated in FITC-bound annexin and propidium iodide (PI) for 15 minutes, and annexin and PI binding were then measured by flow cytometry to acquire data using a BD Accuri C6 flow cytometer (BD Biosciences) and analyzed with the Accuri C6 analysis program (BD Biosciences)/FlowJo software (FlowJo, LLC.). Cancer cell line death was evaluated using a cleaved caspase-3 antibody (Cell Signaling Technology). As shown in FIGS. 1A to 1C, it was confirmed that the cell death by sorafenib did not increase in both the sorafenib-resistant liver cancer cell lines (e.g., Huh7-SR and SK-Hep-R cell lines).

Figure 2A:
FIGS. 2A and 2B are diagrams showing that orphan nuclear receptor ERRγ increases in the sorafenib-resistant liver cancer cell lines Huh7-R (FIG. 2A) and SK-Hep-R FIG. 2B).
Figure 2B:
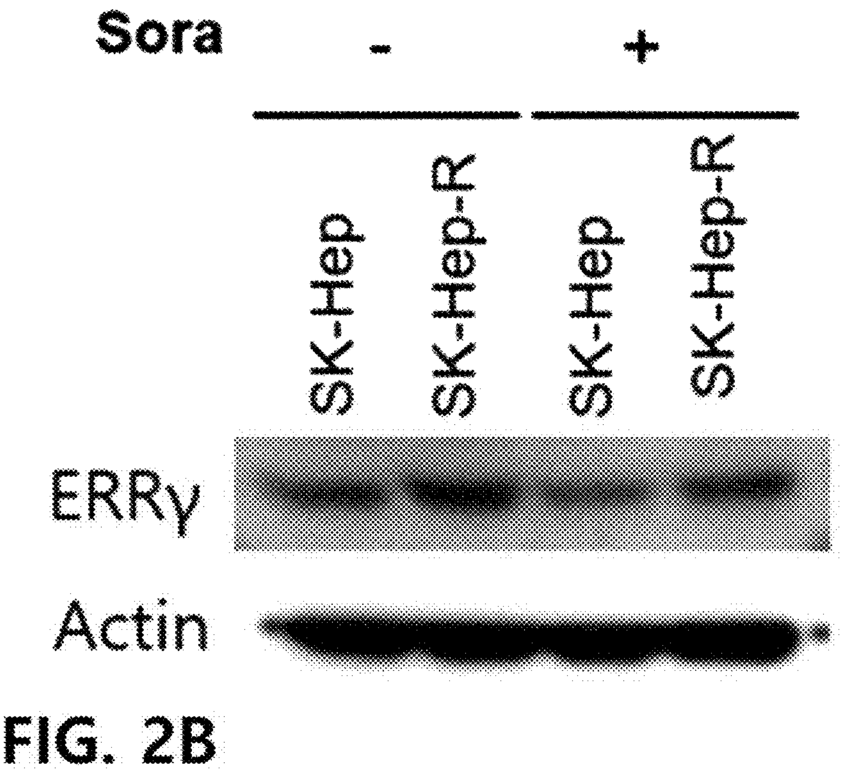

Also, Western blotting was performed to confirm an expression pattern of the orphan nuclear receptor ERRγ in the Huh7-SR and SK-Hep-R cell lines. As a result, it was confirmed that the expression of ERRγ remarkably increased in both of the two sorafenib-resistant liver cancer cell lines, as shown in FIGS. 2A and 2B.

Example 2

Investigation of Effect of Orphan Nuclear Receptor ERRγ on Sorafenib-Resistant Liver Cancer In order to investigate an effect of the compound (DN200434) represented by Formula 1, which is an inverse agonist against ERRγ, on ROS generation in sorafenib-resistant liver cancer cells, the effect was measured by FACS using 2',7'-dichlorohydrofluorescein diacetate (H2-DCF-DA; Invitrogen, USA) as an ROS probe. Drug-resistant cells were treated with sorafenib (10 μM) and the DN200434 compound (12 μM) for 24 hours, and 10 μM H2-DCF-DA was added to the cells. Then, the cells were incubated for 30 minutes, and washed with PBS, and data was collected using a BD Accuri™ C6 flow cytometer (BD Bioscience, USA), and analyzed using an Accuri™ C6 analysis program (BD Bioscience, USA). To determine the number of cells, the sorafenib-resistant liver cancer cell line was treated with the DN200434 compound (12 μM) in combination with sorafenib (10 μM), and stained with trypan blue, and the number of cells was then measured using a hemocytometer.

Figure 3A:
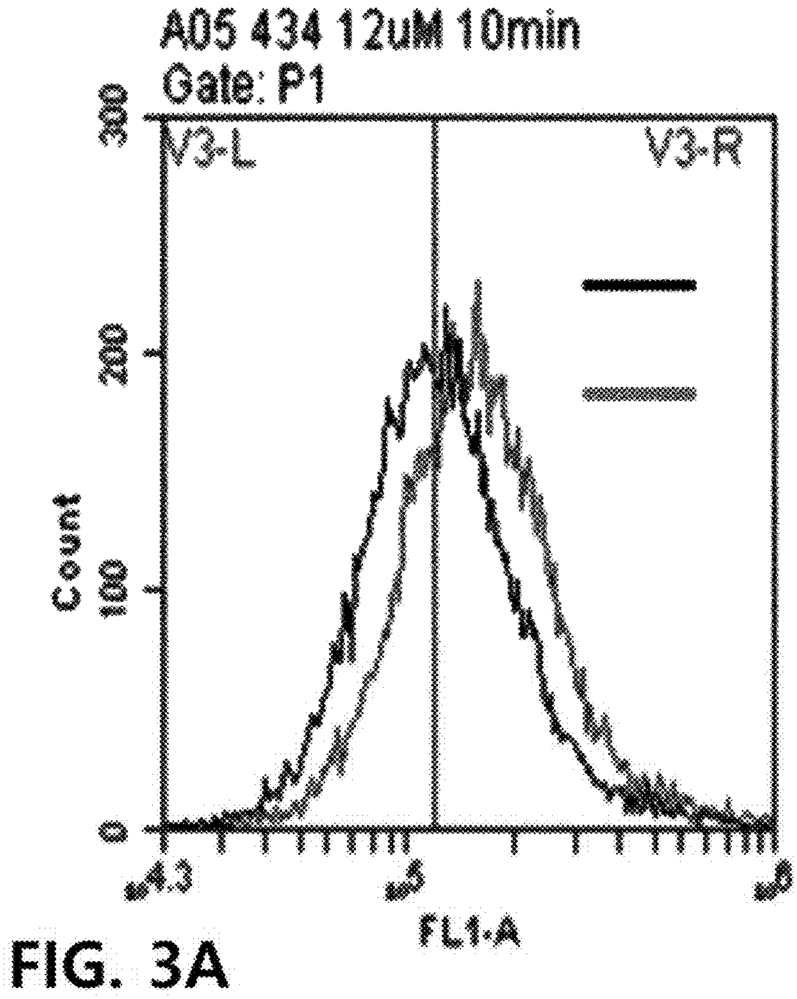
FIGS. 3A and 3B are diagrams showing the results of treating the sorafenib-resistant liver cancer cell lines Huh7-R (FIG. 3A) and SK-Hep-R (FIG. 3B) with a compound (DN200434) of Formula 1 that is an inverse agonist against ERRγ, indicating that reactive oxygen species (ROS) increased in each of the sorafenib-resistant liver cancer cell lines.
Figure 3B:
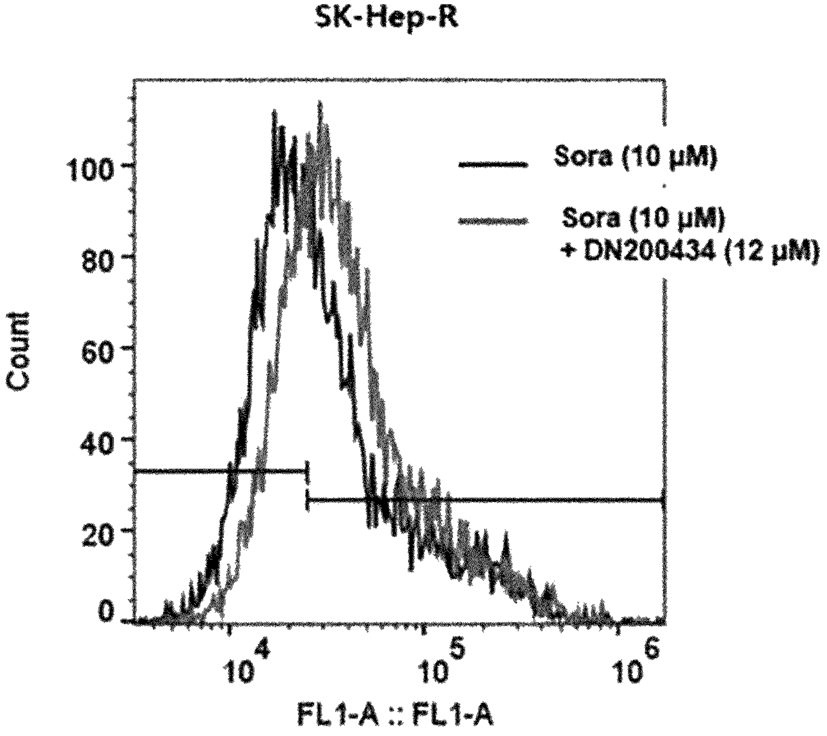
Figure 4A:
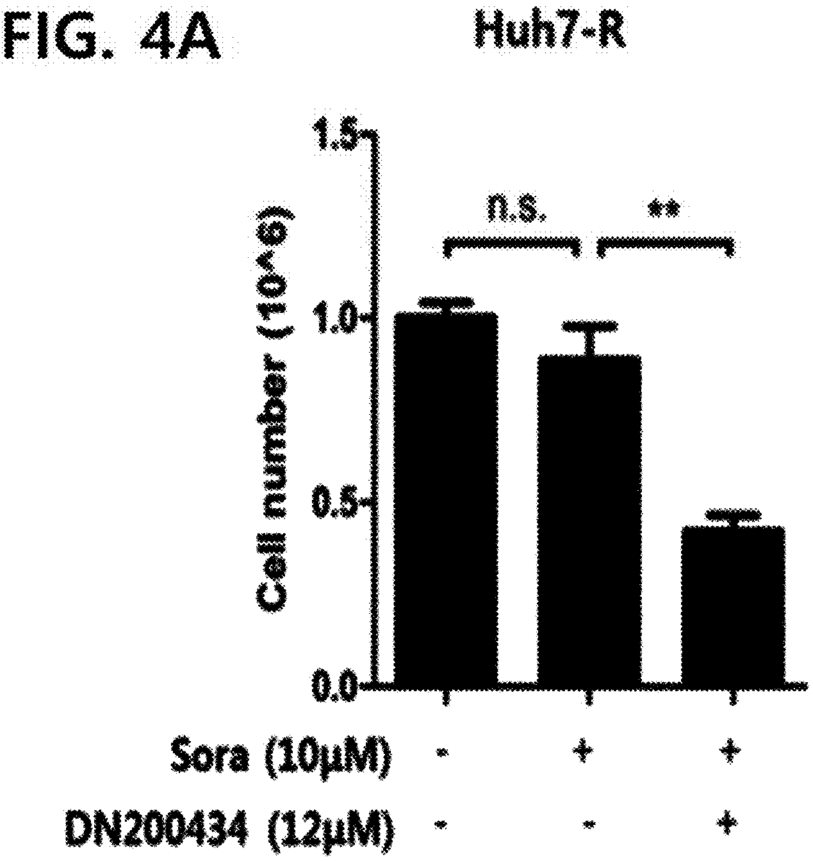
FIGS. 4A and 4B are diagrams showing that the sorafenib-resistant liver cancer cell lines Huh7-R (FIG. 4A) and SK-Hep-R (FIG. 4B) which did not have an anticancer effect when the cell lines are treated with sorafenib alone have reduced cell proliferation when the cell lines are treated with the compound of Formula 1 (DN200434) and sorafenib at the same time.
Figure 4B:
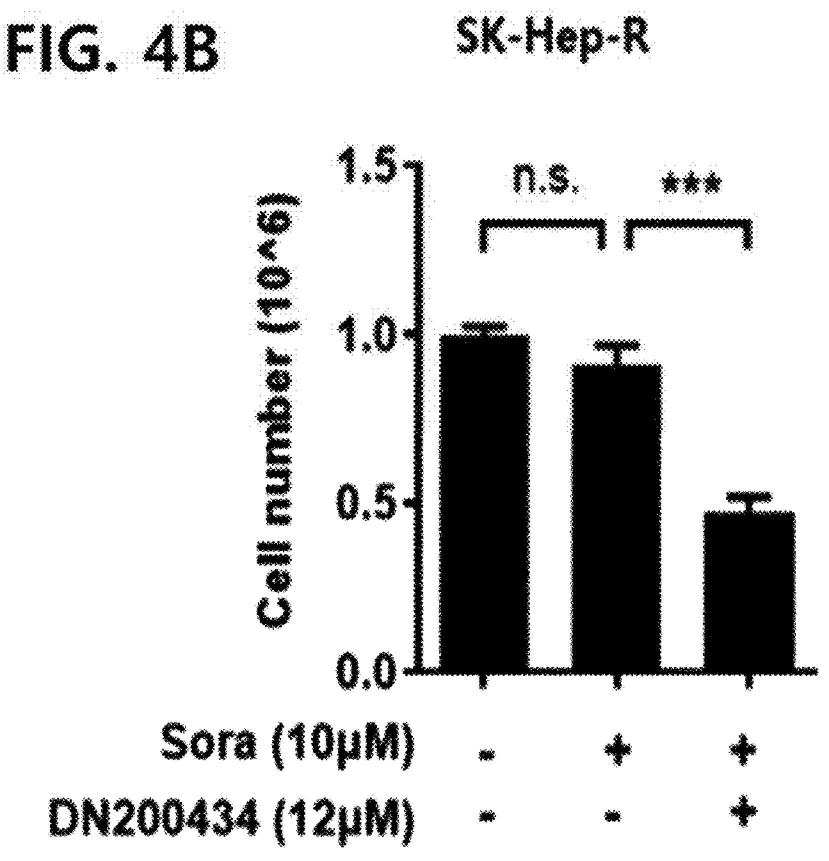

As a result, as shown in FIGS. 3A and 3B, it was confirmed that an increase in ROS by the DN200434 compound was observed in both the Huh7-SR and SK-Hep-R cell lines, which are sorafenib-resistant liver cancer cell lines. As shown in FIGS. 4A and 4B, it was confirmed that the cell proliferation of the sorafenib-resistant liver cancer cells, which was not affected when treated with sorafenib alone, significantly decreased by the simultaneous administration of DN200434 represented by Formula 1. Based on the results as described above, it was confirmed that DN200434 might overcome drug resistance by inhibiting ERRγ activity and increasing the susceptibility to sorafenib.

Example 3

Confirmation of Anticancer Effect in Sorafenib-Resistant Liver Cancer Animal Model The sorafenib-resistant liver cancer cell line Huh7-R was injected into mice in order to construct a sorafenib-resistant liver cancer animal model (xenograft). Thereafter, the inverse agonist against ERRγ (e.g., DN200434 (Formula 1)) was administered in combination with sorafenib, and the size change of the formed mass was measured. In this case, the group in which the sorafenib-resistant liver cancer-derived animal model was treated with sorafenib alone was used as the comparative control.

Figure 5A:
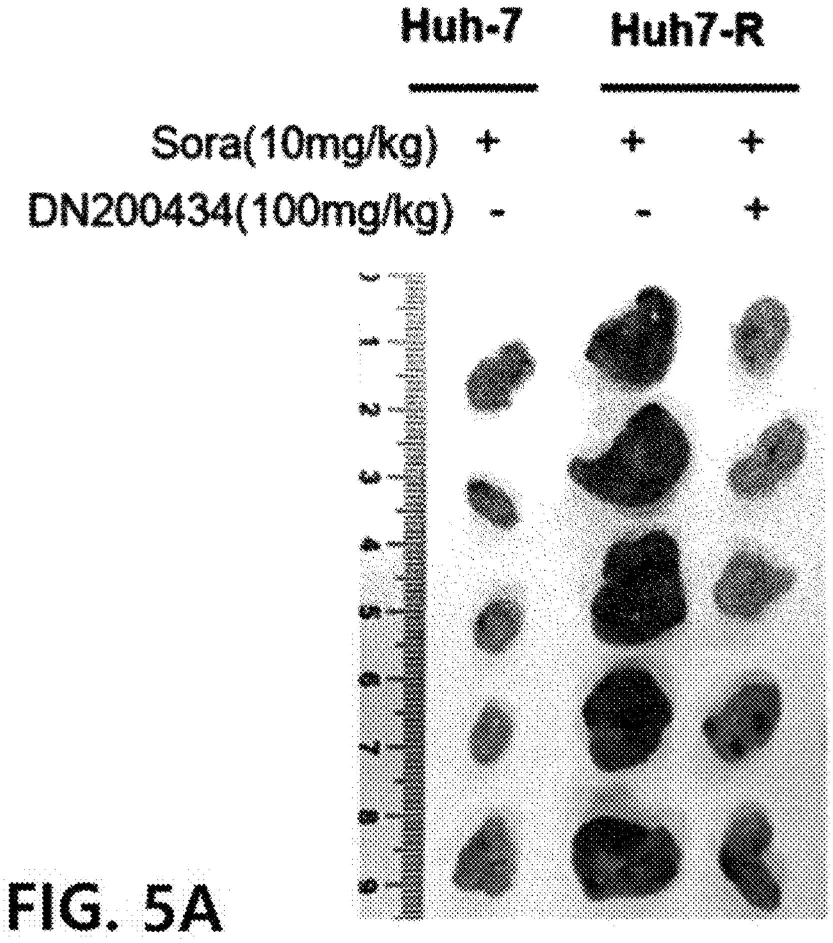
FIG. 5A is an image showing that the size of a tumor remarkably decreases in an animal model (xenograft) derived from the sorafenib-resistant liver cancer cell line Huh7-R when the compound of Formula 1 (DN200434) is administered in combination with sorafenib, compared to the control (a sorafenib-alone-administered group).
Figure 5B:
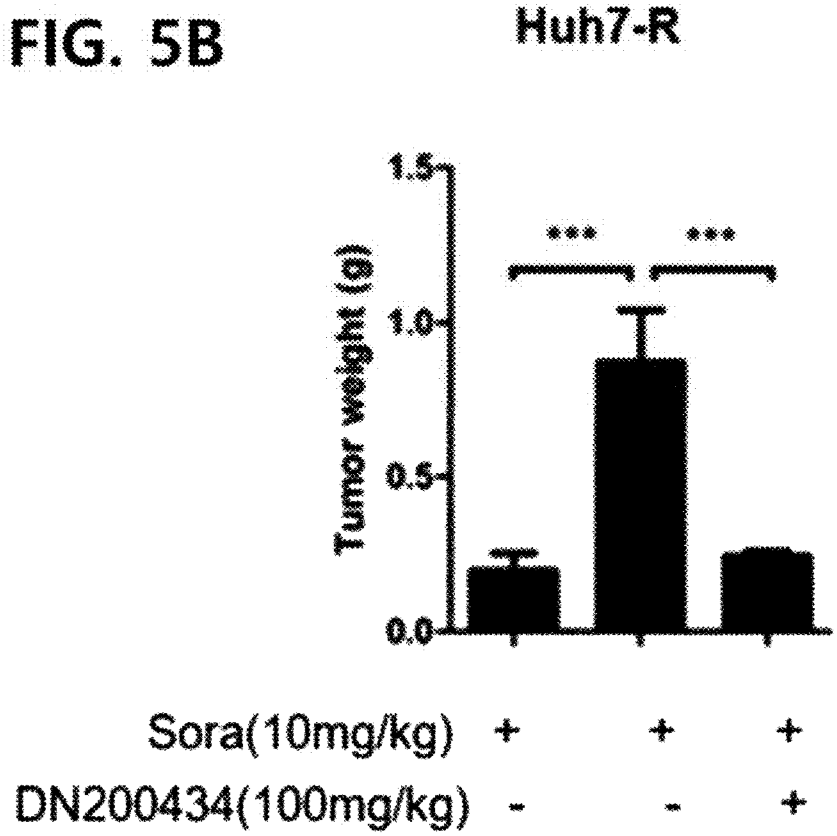
FIG. 5B is a graph showing that the weight of a tumor remarkably decreases in the animal model derived from the sorafenib-resistant liver cancer cell line Huh7-R when the compound of Formula 1 (DN200434) is administered in combination with sorafenib, compared to the control (a sorafenib-alone-administered group).
Figure 5C:
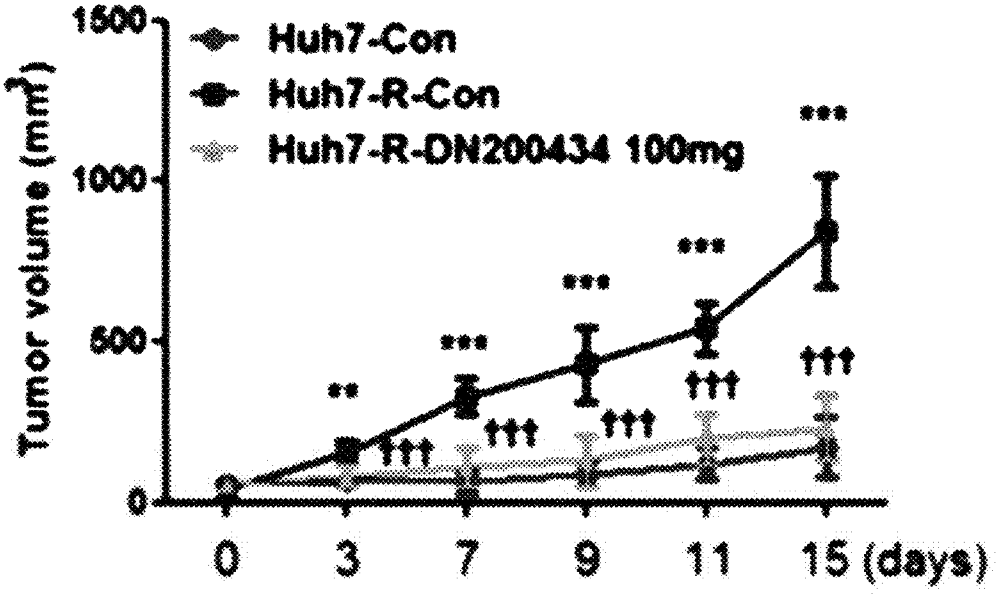
FIG. 5C is a diagram showing that the volume of a tumor remarkably decreases in the animal model derived from the sorafenib-resistant liver cancer cell line Huh7-R when the compound of Formula 1 (DN200434) is administered in combination with sorafenib, compared to the control (Huh7-R-Con; a sorafenib-alone-administered group).
Figure 5D:
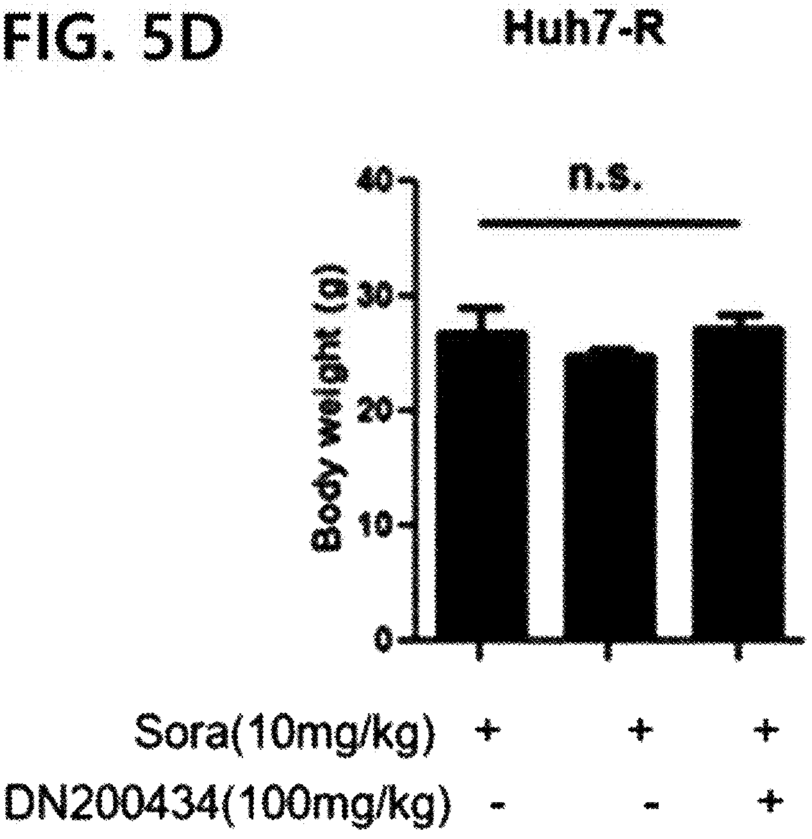
FIG. 5D is a diagram showing that there is no change in body weight between groups as a result of an experiment using the animal model derived from the sorafenib-resistant liver cancer cell line Huh7-R.

As a result, as shown in FIGS. 5A to 5C, it was confirmed that the tumor size, weight and volume significantly decreased in the group in which the DN200434 compound represented by Formula 1, which is an inverse agonist against ERRγ, was administered in combination with sorafenib in the animal model derived from the sorafenib-resistant liver cancer cell line Huh7-R, compared to the control. In this case, as seen from FIG. 5D, it was confirmed that there was no difference in in body weight change between the experimental group and the control.

An animal model derived from the sorafenib-resistant liver cancer cell line SK-Hep-R was constructed in the same manner as described above, and the effect of co-administration of the DN200434 compound represented by Formula 1, which is an inverse agonist against ERRγ, and sorafenib was confirmed.

Figure 6A:
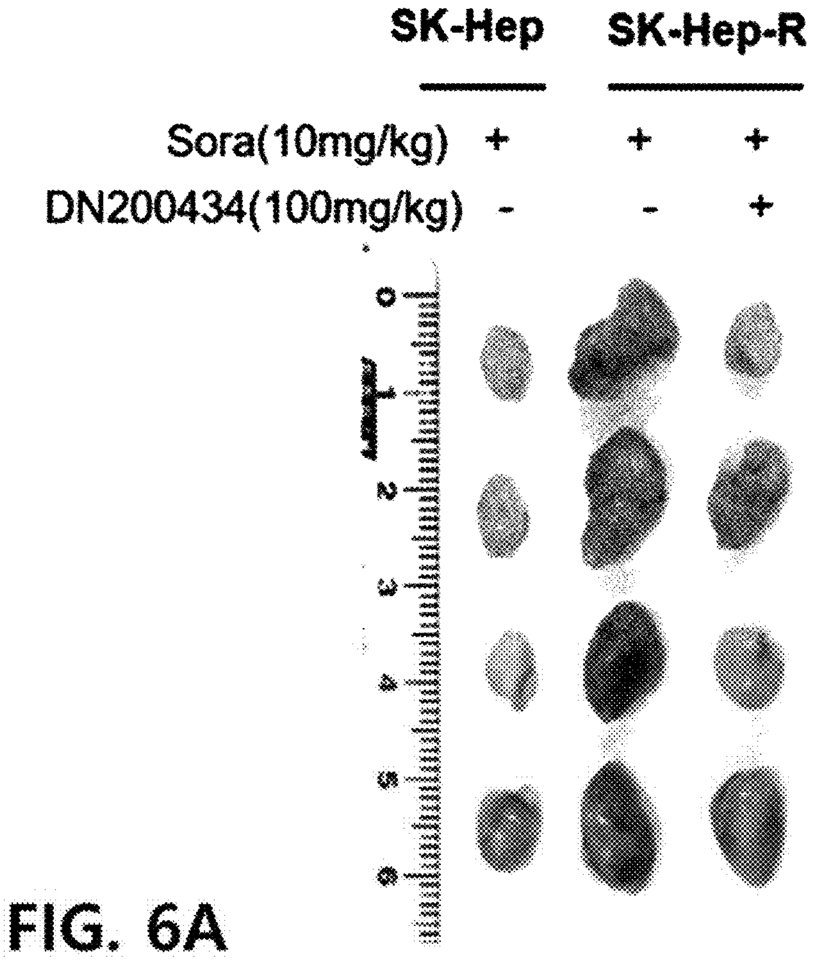
FIG. 6A is an image showing that the size of a tumor remarkably decreases in an animal model (xenograft) derived from the sorafenib-resistant liver cancer cell line SK-Hep-R when the compound of Formula 1 (DN200434) is administered in combination with sorafenib, compared to the control (a sorafenib-alone-administered group).
Figure 6B:
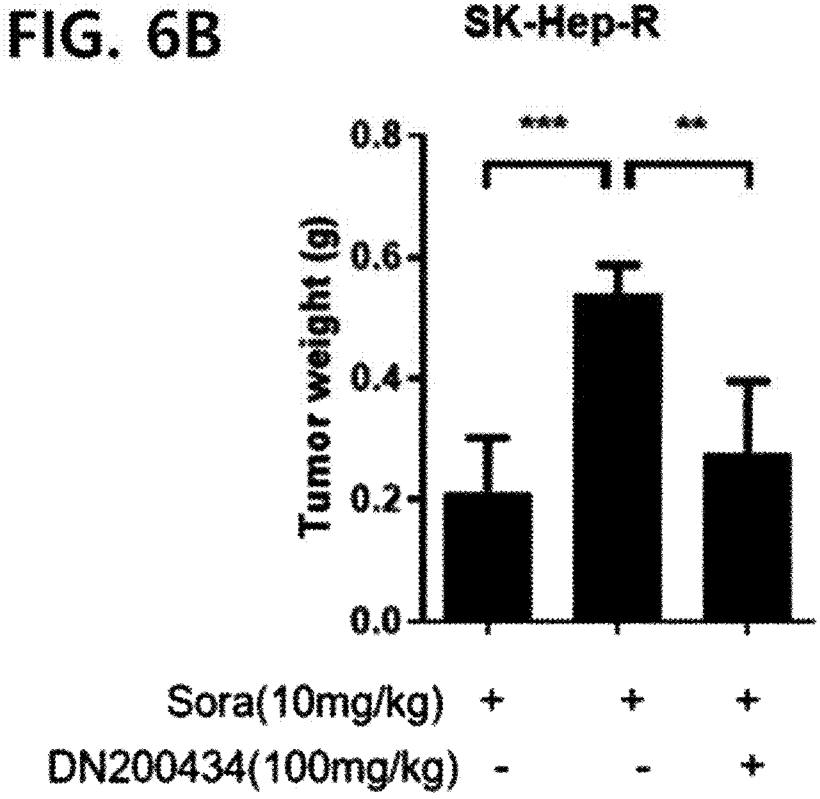
FIG. 6B is a graph showing that the weight of a tumor remarkably decreases in the animal model derived from the sorafenib-resistant liver cancer cell line SK-Hep-R when the compound of Formula 1 (DN200434) is administered in combination with sorafenib, compared to the control (a sorafenib-alone-administered group).
Figure 6C:
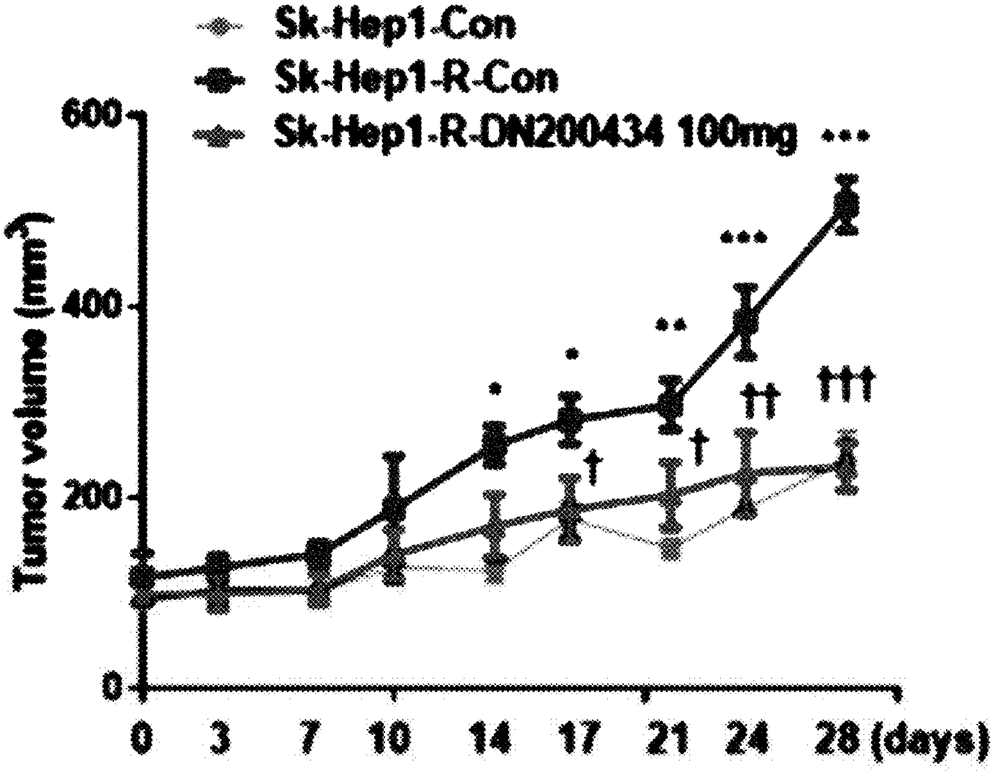
FIG. 6C is a diagram showing that the volume of a tumor remarkably decreases in the animal model derived from the sorafenib-resistant liver cancer cell line SK-Hep-R when the compound of Formula 1 (DN200434) is administered in combination with sorafenib, compared to the control (Huh7-R-Con; a sorafenib-alone-administered group).
Figure 6D:
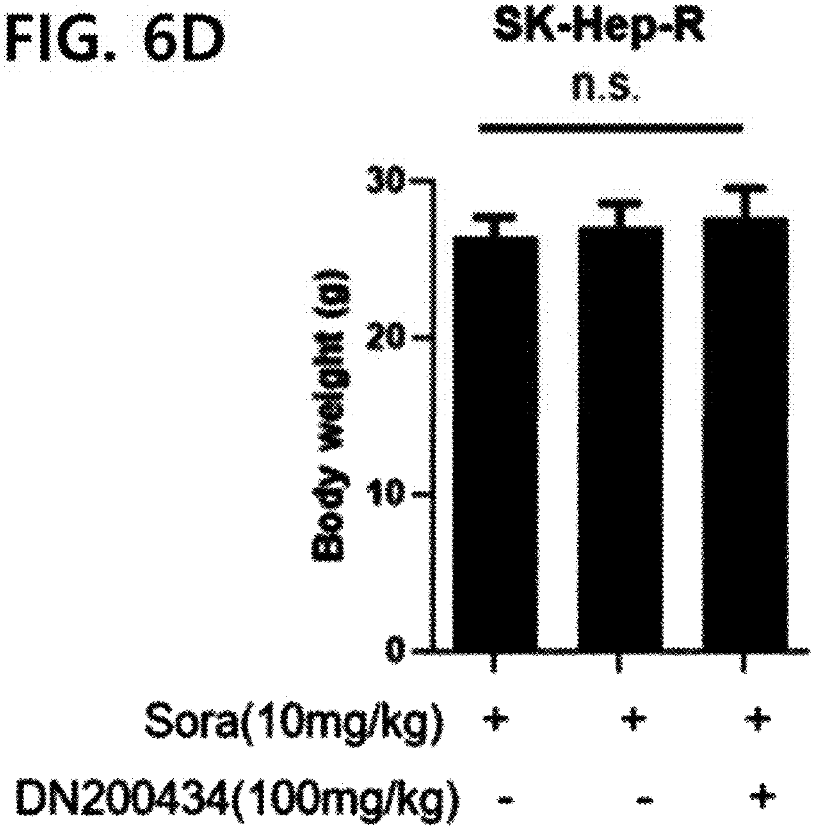
FIG. 6D is a diagram showing that there is no change in body weight between groups as a result of an experiment using the animal model derived from the sorafenib-resistant liver cancer cell line SK-Hep-R.

Similarly, as shown in FIGS. 6A to 6C, it was confirmed that the tumor size, weight, and volume of liver cancer remarkably decreased in the group in which the DN200434 compound was administered in combination with sorafenib even in the animal model derived from the sorafenib-resistant liver cancer cell line SK-Hep-R, compared to the control. As seen from FIG. 6D, it was confirmed that there was no difference in in body weight change between the experimental group and the control.

Putting together the results of Examples 1 to 3, it was confirmed that the expression of ERRγ significantly increased in sorafenib-resistant liver cancer. Also, it was confirmed through the experiments that DN200434, which is an inverse agonist against ERRγ represented by Formula 1, increased intracellular ROS, inhibited the proliferation of the sorafenib-resistant liver cancer cells, and increased the susceptibility to sorafenib. In addition, it was also confirmed that the cancer proliferation significantly decreased, compared to the control, in an animal experiment using a sorafenib-resistant liver cancer cell line. The above results prove that ERRγ plays an important role in drug resistance in liver cancer, and is effective in treating advanced drug-resistant liver cancer when ERRγ activity is inhibited using the DN200434, which is an inverse agonist against ERRγ.

The above description of the present invention is given by way of illustration only, and it should be understood by those skilled in the art to which the present invention belongs that various changes and modifications can be made without departing from the technical spirit and scope of the present invention. Therefore, it should be understood that the aforementioned embodiments are given by way of illustration only, and are not intended to be limiting in all aspects.

The invention claimed is:

1. A method for diagnosis and treatment of sorafenib-resistant liver cancer, comprising the following steps:

(a) measuring an expression level of mRNA of an estrogen-related receptor γ (ERRγ) gene or a protein expressed therefrom in a biological sample isolated from a test patient with liver cancer;

(b) comparing the measured expression level of the ERRγ mRNA and/or the measured level of ERRγ protein of the test patient of step (a) with a reference expression level of ERRγ mRNA and/or a reference level of ERRγ protein, said reference expression level of ERRY mRNA and/or a reference level of ERRγ protein being obtained from a reference patient with a liver cancer other than sorafenib-resistant liver cancer, wherein a higher measured expression level of the ERRγ mRNA than the reference expression level and/or a higher measured level of ERRγ protein than the reference level indicates that the test patient has sorafenib-resistant liver cancer; and (c) administering to the test patent who is determined to have sorafenib-resistant liver cancer, (i) an agent capable of inhibiting ERRγ protein activity or ERRγ gene expression; (ii) a combination of sorafenib and an agent capable of inhibiting ERRγ protein activity or ERRγ gene expression.

2. The method of claim 1, wherein the biological sample comprises liver tissue, liver cells, whole blood, plasma, or serum.

3. A method selected from the group consisting of:

(a) preventing or inhibiting a development of sorafenib resistance in a liver cancer patient who is prescribed for sorafenib treatment or underwent sorafenib treatment; and (b) enhancing sorafenib treatment of a liver cancer patient, said method comprising administering to the liver cancer patient an effective amount of an inverse agonist against estrogen-related receptor γ (ERRγ), wherein the inverse agonist against ERRγ is a compound of the following Formula 1 or a pharmaceutically acceptable salt thereof:

[Formula 1]

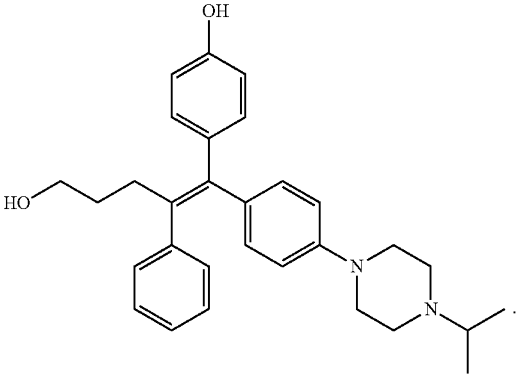

4. The method of claim 3, which further comprises administering sorafenib, wherein the inverse agonist is administered simultaneously with sorafenib, separately, or sequentially.

5. A method of treating liver cancer in a subject in need thereof, comprising:

administering an effective amount of an inverse agonist against estrogen-related receptor γ (ERRγ), wherein the inverse agonist against ERRγ is a compound of the following Formula 1 or a pharmaceutically acceptable salt thereof:

[Formula 1]

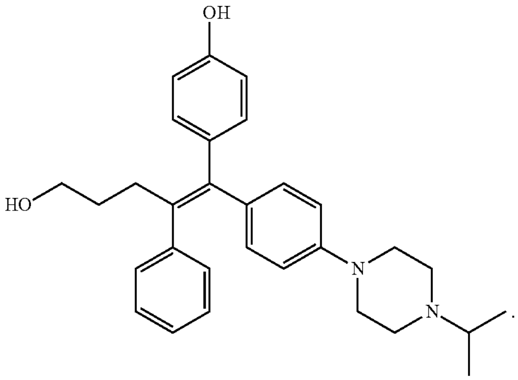

6. The method of claim 1, wherein the agent is administered simultaneously with sorafenib, separately, or sequentially.

7. The method of claim 5, wherein the inverse agonist is administered simultaneously with sorafenib, separately, or sequentially.

* * * * *